United States Patent
Wang et al.

(10) Patent No.: US 10,577,295 B2
(45) Date of Patent: *Mar. 3, 2020

(54) PROCESS FOR PRODUCING CHLOROTRIFLUOROETHYLENE

(71) Applicant: HONEYWELL INTERNATIONAL INC., Morris Plains, NJ (US)

(72) Inventors: Haiyou Wang, Amherst, NY (US); Hsueh Sung Tung, Getzville, NY (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/852,794

(22) Filed: Dec. 22, 2017

(65) Prior Publication Data

US 2019/0002374 A1    Jan. 3, 2019

Related U.S. Application Data

(63) Continuation of application No. 14/843,076, filed on Sep. 2, 2015, now Pat. No. 9,850,188.

(60) Provisional application No. 62/046,340, filed on Sep. 5, 2014.

(51) Int. Cl.

| | | |
|---|---|---|
| *C07C 17/25* | (2006.01) | |
| *C07C 21/18* | (2006.01) | |
| *B01J 27/128* | (2006.01) | |
| *B01J 27/132* | (2006.01) | |
| *B01J 27/10* | (2006.01) | |
| *B01J 27/06* | (2006.01) | |
| *B01J 27/12* | (2006.01) | |
| *B01J 27/138* | (2006.01) | |
| *B01J 21/18* | (2006.01) | |
| *B01J 21/10* | (2006.01) | |
| *B01J 21/04* | (2006.01) | |

(52) U.S. Cl.
CPC ............ *C07C 17/25* (2013.01); *B01J 27/06* (2013.01); *B01J 27/10* (2013.01); *B01J 27/12* (2013.01); *B01J 27/128* (2013.01); *B01J 27/132* (2013.01); *B01J 21/04* (2013.01); *B01J 21/10* (2013.01); *B01J 21/18* (2013.01); *B01J 27/138* (2013.01); *B01J 2523/11* (2013.01); *B01J 2523/12* (2013.01); *B01J 2523/13* (2013.01); *B01J 2523/15* (2013.01); *B01J 2523/17* (2013.01); *B01J 2523/22* (2013.01); *B01J 2523/23* (2013.01); *B01J 2523/27* (2013.01); *B01J 2523/67* (2013.01); *B01J 2523/68* (2013.01); *B01J 2523/72* (2013.01); *B01J 2523/821* (2013.01); *B01J 2523/824* (2013.01); *B01J 2523/825* (2013.01); *B01J 2523/827* (2013.01); *B01J 2523/828* (2013.01); *B01J 2523/842* (2013.01); *B01J 2523/845* (2013.01); *B01J 2523/847* (2013.01)

(58) Field of Classification Search
CPC ...................................................... C07C 17/25
See application file for complete search history.

(56) References Cited

U.S. PATENT DOCUMENTS

| | | | |
|---|---|---|---|
| 2009/0043136 A1* | 2/2009 | Wang ................. | B01J 27/10 570/136 |
| 2010/0324345 A1* | 12/2010 | Bektesevic ............ | C07C 17/25 570/156 |

* cited by examiner

*Primary Examiner* — Medhanit W Bahta
(74) *Attorney, Agent, or Firm* — Fox Rothschild LLP

(57) ABSTRACT

The present invention relates, at least in part, to a process for making chlorotrifluoroethylene (CFO-1113) from 1,2-dichloro-1,1,2-trifluoroethane (HCFC-123a). In certain aspects, the process includes dehydrochlorinating 1,2-dichloro-1,1,2-trifluoroethane (HCFC-123a) in the presence of a catalyst selected from the group consisting of (i) one or more metal halides; (ii) one or more halogenated metal oxides; (iii) one or more zero-valent metals or metal alloys; (iv) combinations thereof.

23 Claims, No Drawings

PROCESS FOR PRODUCING CHLOROTRIFLUOROETHYLENE

CROSS REFERENCE TO RELATED APPLICATIONS

The present invention is a continuation of U.S. application Ser. No. 14/843,076, filed Sep. 2, 2015, (now pending), which application relates to and claims the priority benefit of U.S. Application 62/046,340, filed Sep. 4, 2014, which is incorporated herein by reference in its entirety as is fully set forth below.

FIELD OF THE INVENTION

The present invention relates, at least in part, to a process for making chlorotrifluoroethylene (CFO-1113) from 1,2-dichloro-1,1,2-trifluoroethane (HCFC-123a).

BACKGROUND OF THE INVENTION 1-chloro-1,2,2-trifluoroethylene (also named as chlorotrifluoroethylene (CTFE) or CFO-1113) is commonly used as a refrigerant in cryogenic applications. CFO-1113 has a carbon-carbon double bond and so can be polymerized to form polychlorotrifluoroethylene or copolymerized to produce the plastic ECTFE. Chlorotrifluoroethylene (CFO-1113) is currently manufactured commercially by dechlorinating 1,1,2-trichlorotrifluoroethane (CFC-113) via reaction with zinc in the presence of methanol as a solvent. A major drawback with this process is the formation of 1,2-dichloro-1,1,2-trifluoroethane (HCFC-123a) as a major byproduct, which greatly reduces the yield of CFO-1113 and is also costly to dispose of.

Applicants have come to appreciate that it would be desirable to develop a method which is able to convert HCFC-123a to a more useful product, including specifically CFO-1112. One route which has been contemplated by applicants for producing CFO-1113 from HCFC-123a is through its dehydrochlorination either in the presence of a caustic solution in a liquid phase reaction or more preferably in the presence of a solid catalyst in a vapor phase reaction. One potential problem that may be associated with certain vapor phase processes is the formation of by-products such as trans- and/or cis-isomers of 1,2-dichloro-1,2-difluoroethylene (CFO-1112) which can be formed via a competing dehydrofluorination reaction. The formation of these byproducts in significant quantities can negatively reduce the yield of the desired CFO-1112 product and can negatively effect the process efficiency due to additional requirements for product separation. Applicants have therefore comet to appreciate that it would be advantageous to develop processes and systems, including catalyst systems, that are able to reduce or suppress the extent of undesirable dehydrofluorination reactions and to increase the productivity and yield of the desired fluorinated olefin, namely, CFO-1113.

SUMMARY OF THE INVENTION

In certain non-limiting aspects, the present invention provides processes for making chlorotrifluoroethylene (CFO-1113) from 1,2-dichloro-1,1,2-trifluoroethane (HCFC-123a). In certain embodiments, the processes include dehydrochlorinating 1,2-dichloro-1,1,2-trifluoroethane (HCFC-123a) in the presence of a catalyst selected from the group consisting of (i) one or more metal halides; (ii) one or more halogenated metal oxides; (iii) one or more zero-valent metals or metal alloys; and (iv) combinations thereof. This reaction can be depicted schematically as follows:

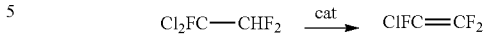

Preferably, the processes provides a conversion percentage of HCFC-123a that is at least about 5 wt. %, more preferably in certain embodiments at least about 10 wt. %, and even more preferably in certain embodiments at least about 15 wt. %. In certain preferred embodiments, include in accordance with each of the preferred conversion percentages mentioned herein, the selectivity of the process to chlorotrifluoroethylene is at least about 70 wt. %, more preferably in certain embodiments at least about 80 wt. %, and even more preferably in certain embodiments at least about 90 wt. %.

The reaction product stream of the dehydrochlorinating step, that is, prior to any distillation or purification, in certain embodiments preferably includes less than about 10 wt. % of organic by-product impurities, more preferably in certain embodiments less than about 7 wt. % of organic by-product impurities, and in even more preferably in certain embodiments less than about 5% organic by-product impurities. In certain embodiments, the reaction product stream, prior to any distillation or purification, preferably includes less than about 10 wt. % of the organic by-product impurity CFO-1112, more preferably in certain embodiments less than about 7 wt. % of CFO-1112, and in even more preferably in certain embodiments less than about 5 wt. % of CFO-1112. As used herein, the term "organic by-product impurities" means organic products other than the starting reactants, including HCFC-123a but does not include by-product acid gas, such as HCl or HF.

The dehydrochlorinating step may be conducted under reaction conditions, including temperature, pressure and reaction time conditions, that results in the desired CFO-1113 product and preferably one or more of the advantages discussed herein. In certain preferred embodiments, the process comprises conducting the dehydrochlorination at a temperature greater than about 400° C., more preferably in certain embodiments greater than about 425° C., and even more preferably in certain embodiments greater than about 450° C. In certain aspects, at least a substantial portion of the dehydrochlorination reaction, and preferably in certain embodiment substantially the entire dehydrochlorination reaction, is conducted within a temperature range of from about 400° C. to about 550° C., and more preferably in certain embodiments within a temperature range of from about 425° C. to about 550° C., and even more preferably in certain embodiments within a temperature range of from about 480° C. to about 550° C. In certain preferred embodiments, at least a substantial portion of the dehydrochlorination reaction, and preferably in certain embodiment substantially the entire dehydrochlorination reaction, is conducted within a temperature range of from about 480° C. to about 525° C.

In certain preferred embodiments, the catalyst includes mono-valent metal halide, bi-valent metal halide, tri-valent metal halide, or a combination thereof. The catalyst can be supported or unsupported, although supported catalyst systems are preferred in certain embodiments. The component metal in such preferred embodiments may include one or more of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. The component halogen may include one or more of $F^-$, $Cl^-$, $Br^-$, and $I^-$. Non-limiting examples of such catalysts include one or more of LiF, NaF, KF, CsF, $MgF_2$, $CaF_2$, LiCl, NaCl, KCl, and CsCl. In certain embodiments, the catalyst includes an optionally supported combination of $MgF_2$ and one or more of CsCl, LiCl, NaCl, KCl, LiF, NaF, KF, and/or CsF. In certain preferred embodiments of the foregoing combination, the one or more of CsCl, LiCl, NaCl, KCl, LiF, NaF, KF, and/or CsF is present in an amount of about 5.0 wt. % to about 50 wt %, based on the total weight of the catalyst in combination with $MgF_2$.

In further embodiments, the catalyst may include one or more of an optionally substituted halogenated mono-valent metal oxide, halogenated bi-valent metal oxide, halogenated tri-valent metal oxide, or a combination thereof. In such embodiments, the component metal may include one or more of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Non-limiting examples of such catalysts include at least one optionally supported halogenated metal oxide selected from the group consisting of fluorinated or chlorinated MgO, fluorinated or chlorinated CaO, fluorinated or chlorinated $Li_2O$, fluorinated or chlorinated $Na_2O$, fluorinated or chlorinated $K_2O$, and fluorinated or chlorinated $Cs_2O$. In certain aspects, the catalyst includes an optionally supported combination of fluorinated MgO with one or more of a fluorinated $Cs_2O$, a fluorinated $Li_2O$, a fluorinated $Na_2O$, and/or a fluorinated $K_2O$. In certain aspects of such a combination, the one or more of a fluorinated $Cs_2O$, a fluorinated $Li_2O$, a fluorinated $Na_2O$, and/or a fluorinated $K_2O$ may be present in an amount of about 5.0 wt. % to about 50 wt %, based on the total weight of the catalyst in combination with MgO.

In even further embodiments, the catalyst comprises an optionally supported zero valent metal, a zero valent metal alloy, or a combination thereof. In such embodiments, the component metal may include one or more of Pd, Pt, Rh, Ru, Ir, Os, Fe, Co, Ni, Cu, Mo, Cr, and Mn. Zero valent metal alloys may include one or more stainless steel alloys, Monel alloys, Inconel alloys, Hastelloy alloys, Incoloy alloys and combinations thereof. Catalyst supports may include, but are not limited to, MgO, fluorinated MgO, $MgF_2$, carbon materials such as activated carbons and carbon molecular sieves, and $\alpha$-$Al_2O_3$. In certain preferred embodiments, the zero valent metal or zero valent metal alloy comprises one or more of Pd, Pt, Ru, Rh, and/or Ir supported on MgO. In certain preferred embodiments of such a preferred combination, the one or more of Pd, Pt, Ru, Rh, and/or Ir may be present in an amount of about 0.05 to about 5 wt %, based on the total weight of the catalyst in combination with MgO. In further embodiments, the catalyst is a zero valent metal alloy that is contained within the walls of the reactor.

Additional embodiments and advantages will be readily apparent to one of skill in the art on the basis of the disclosure provided herein.

DETAILED DESCRIPTION OF THE INVENTION

In the present invention, 1,2-dichloro-1,1,2-trifluoroethane (HCFC-123a) is dehydrochlorinated in the presence of a catalyst to form a product comprising chlorotrifluoroethylene (CFO-1113).

In the process of the present invention, the catalysts are preferably selected to achieve the selectivity and/or conversion of HCFC-123a to CFO-1113 according to one or more of the preferred embodiments described herein. The processes of the present invention preferably utilize catalysts as described herein since applicants have found that such catalysts are capable, especially and preferably under the other reaction conditions specified herein, of providing advantageous selectivity for the dehydrochlorination reaction than for competing reactions, including dehydrofluorination side reaction(s).

There are three preferred classes of catalysts that applicants have found to be especially useful in the present invention: (i) metal halides, (ii) halogenated metal oxides, and (iii) zero-valent metals/metal alloys.

The first class of catalysts is metal halides. In certain preferred embodiments, the metal halides include mono-, bi-, and tri-valent metal halides and their mixtures/combinations, and in certain more preferred embodiments mono- and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of preferred mono- or bi-valent metal halides include, but are not limited to, LiF, NaF, KF, CsF, $MgF_2$, $CaF_2$, LiCl, NaCl, KCl, and CsCl. The catalyst may be supported or unsupported, such as with one or a combination of catalyst supports discussed herein. In certain embodiments, the catalyst is a combination of $MgF_2$ with one or more of CsCl, LiCl, NaCl, KCl, LiF, NaF, KF, and/or CsF. In certain aspects of such embodiments, CsCl, LiCl, NaCl, KCl, LiF, NaF, KF, and/or CsF are present in an amount of about 5.0 to about 50 wt %, based on the total weight of the catalyst.

The second class of catalysts is halogenated metal oxides. In certain preferred embodiments, the halogenated metal oxides include halogenated mono-, bi-, and tri-valent metal oxides and their mixtures/combinations, and in certain more preferred embodiments halogenated mono- and bi-valent metal oxides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Halogenation treatments can include any of those known in the prior art, particularly those that employ HF, $F_2$, HCl, $Cl_2$, HBr, $Br_2$, HI, and $I_2$ as the halogenation source. Examples of preferred halogenated mono- and bi-valent metal oxides include, but are not limited to, fluorinated or chlorinated MgO, fluorinated or chlorinated CaO, fluorinated or chlorinated $Li_2O$, fluorinated or chlorinated $Na_2O$, fluorinated or chlorinated $K_2O$, and fluorinated or chlorinated $Cs_2O$. The catalyst may be supported or unsupported, such as with one or a combination of catalyst supports discussed herein. In certain embodiments, the catalyst includes a combination of fluorinated MgO with one or more of a fluorinated $Cs_2O$, a fluorinated $Li_2O$, a fluorinated $Na_2O$, and/or a fluorinated $K_2O$. In certain aspects of such embodiments, the fluorinated $Cs_2O$, fluorinated $Li_2O$, fluorinated $Na_2O$, and/or fluorinated $K_2O$ is present in an amount of about 5.0 to about 50 wt %, based on the total weight of the catalyst.

The third class of catalysts is neutral (i.e., zero valent) metals, metal alloys, and their mixtures. The zero valent metals may include, but are not limited to, Pd, Pt, Rh, Ru, Ir, Os, Fe, Co, Ni, Cu, Mo, Cr, Mn, and combinations of the foregoing as alloys or mixtures. The catalyst may be supported or unsupported. Useful supports include, but are not limited to MgO, fluorinated MgO, $MgF_2$, carbon materials such as activated carbons and carbon molecular sieves, $\alpha$-$Al_2O_3$. In certain embodiments, the catalyst includes a combination of MgO with one or more of Pd, Pt, Ru, Rh, and/or Ir. In certain aspects of such embodiments, Pd, Pt, Ru, Rh, and/or Ir are present in an amount of about 0.05 to about 5 wt %, based on the total weight of the catalyst.

Non-limiting examples of metal alloys include stainless steel alloys (304, 316, 316L, etc.), Monel alloys (400, 401, 404, etc.), Inconel alloys (600, 617, 625, 718, etc.), Hastelloy alloys (B-2, C-4, C-22, C-276, etc.), and Incoloy alloys (800, 825, etc.). In certain preferred embodiments, the metal alloy catalyst is an Inconel alloy. In certain preferred embodiments, the catalyst is an Inconel 625 alloy. In one preferred embodiment, a surface of a metal alloy reactor vessel, and in preferred embodiments an inner surface of the vessel can serve as catalyst for HCFC-123a dehydrochlorination.

In addition to CFO-1113, the reaction product mixture may also have unconverted HCFC-123a and hydrogen chloride. In certain aspects, the final reaction product contains, prior to any distillation or purification, less than about 10 wt. % of organic by-product impurities, less than about 7 wt. % of organic by-product impurities, or less than about 5 wt. % of organic by-product impurities, based on the total weight of the final product. Such organic by-product impurities may include any one or more compounds that inhibit the ability to convert HCFC-123a and/or the production (e.g. selectivity of) chlorotrifluoroethylene (CFO-1113), particularly at the levels discussed in greater detail below. In one embodiment, such organic by-product impurities include, but are not limited to, CFO-1112 isomers (e.g. 1,2-dichloro-1,2-difluoroethylene), HFO-1123 (1,1,2-trifluoroethene), CFC-13 (chlorotrifluoromethane), CFC-12 (dichlorodifluoromethane), and G-124 isomer (2-chloro-1,1,1,2-tetrafluoroethane). In certain preferred embodiments, the organic by-product impurities include CFO-1112 isomers, particularly 1,2-dichloro-1,2-difluoroethylene.

According to certain preferred embodiments, the reaction product stream, prior to any distillation or purification, includes less than about 10 wt. % of CFO-1112, more preferably less than about 7 wt. % of CFO-1112, and even more preferably less than about 5 wt. % of CFO-1112, based on the total weight of the components in the reaction product stream. In certain preferred embodiments, the reaction of the present invention is conducted under conditions effective to ensure that the amount of organic by-product impurities, and preferably in certain embodiments, CFO-1112, is reduced prior to any purification or distillation, relative to the amount of impurities produced by reaction conditions that lie outside each of those preferred reaction conditions disclosed herein.

Greatly enhanced or improved selectivity for CFO-113 is an unexpected but highly advantageous feature of the preferred aspects of the present invention. The dehydrochlorination reaction is, in certain preferred embodiments, preferably carried out under conditions effective to obtain a selectivity of at least about 70%, more preferably at least about 80%, and most preferably at least about 90%. The dehydrochlorination reaction is, in certain preferred embodiments, preferably carried out under conditions effective to obtain a conversion of at least about 5%, more preferably at least about 10%, and even more preferably at least about 15%. In certain highly preferred embodiments, the dehydrochlorination reaction is carried out under conditions effective to at once obtain a selectivity and a conversion according to any one of the preferred aspects described herein.

The dehydrochlorinating step may be conducted at any temperature and pressure that results in the product and preferably the advantages discussed herein. In certain aspects, dehydrochlorination may be carried out at a temperature range of about 200° C. to about 800° C., and in certain embodiments from about 300° C. to about 600° C. In certain embodiments, the temperature is about or greater than 400° C., about or greater than 425° C., or about or greater than 450° C. In further embodiments, the temperature is within the range of from about 425° C. to about 525° C. in the presence of a catalyst. In certain aspects, the dehydrochlorinating step is conducted within a temperature range of from about 425° C. to about 550° C. In further aspects, the dehydrochlorinating step is conducted within a temperature range of from about 480° C. to about 550° C., and in further aspects, the dehydrochlorinating step is conducted within a temperature range of from about 480° C. to about 525° C.

It is contemplated that a variety of reaction pressures may be used, such as superatmospheric, atmospheric, and subatmospheric. In certain aspects, atmospheric pressure is preferred.

Dehydrochlorination may optionally be carried out in presence or absence of an oxidizing agent. Useful examples of oxidizing agents include, but are not limited to, oxygen and carbon dioxide. Use of an oxidizing agent can extend the life of the catalyst. The oxidizing agent can be pure or diluted with an inert gas such as nitrogen before being introduced into reactor. The level of oxidizing agent is generally from about 1% to about 10% by volume and preferably from about 2% to 5% by volume based on the volume of the organic feed.

It may also be advantageous to periodically regenerate the catalyst after prolonged use while in place in the reactor. Regeneration of the catalyst may be accomplished by any means known in the art. One method is by passing oxygen or oxygen diluted with nitrogen over the catalyst at temperatures of about 200° C. to about 600° C. (in certain preferred embodiments from about 350° C. to about 450° C.) for about 0.5 hour to about 3 days followed by either halogenation treatment at temperatures of about 25° C. to about 400° C. (in certain preferred embodiments from about 200° C. to about 350° C.) for halogenated metal oxide catalysts and metal halide ones or reduction treatment at temperatures of about 100° C. to about 600° C. (preferably about 200° C. to about 350° C.) for metal catalysts.

Dehydrochlorination is preferably carried out in a corrosion-resistant reaction vessel. Examples of corrosion-resistant materials are Hastelloy, Inconel, Monel and fluoropolymer linings. The vessel may have a fixed and/or a fluidized catalyst bed. If desired, inert gases such as nitrogen or argon may be employed in the reactor during operation.

EXAMPLES

The following are examples of the present invention and are not to be construed as limiting.

Example 1

About 40 ml of 10% $CsCl/MgF_2$ catalyst was charged into a ¾"×0.035" tube Inconel 625 reactor. The reactor was installed in the middle of an electric 3-zone split furnace. Process temperatures were recorded using a multi-point thermocouple placed inside the reactor and within the catalyst bed. The reactor was firstly heated to desired temperatures in nitrogen flow, and then a stream containing 94.6% pure HCFC-123a was fed into the bottom of the vertically mounted reactor at a feed rate of 12 g/h to start a reaction. The reactor pressure was set at 1 atm. The reactor effluent was periodically sampled and analyzed by GC-MS and GC for its compositions to determine raw material conversion level and product selectivity.

As shown in Table 1, both HCFC-123a conversion and CFO-1113 selectivity were increased with increasing temperature over the 10% $CsCl/MgF_2$ catalyst. At 500° C., on average, the HCFC-123a conversion and CFO-1113 selectivity were 16.2 and 96.7%, respectively. As a comparison, the empty Inconel 625 reactor provided a conversion of about 6% and a CFO-1113 selectivity of about 94% at the same 500° C.

TABLE 1

HCFC-123a dehydrochlorination[1]

| Catalyst | Temperature, ° C. | HCFC-123a conv., % | Selectivity, % CFO-1113 | Others[2] |
|---|---|---|---|---|
| 10% CsCl/MgF$_2$ | 450 | 5.0 | 77.2 | 22.8 |
|  | 480 | 8.8 | 82.9 | 17.1 |
|  | 500 | 16.2 | 96.7 | 3.3 |
| Inconel 625 (empty tube) | 500 | 6.5 | 93.9 | 6.1 |

[1]Other reaction conditions: 0 psig, 94.6% pure 123a feed, 12 g/h feed rate;
[2]Others include CFO-1112 isomers, HFO-1123, CFC-13, CFC-12, G-124 isomer, etc.

The above experimental protocol is performed using the following catalysts: 10% LiCl/MgF$_2$, 10% NaCl/MgF$_2$, 10% KCl/MgF$_2$, 10% LiF/MgF$_2$, 10% NaF/MgF$_2$, 10% KF/MgF$_2$, and 10% CsF/MgF$_2$. At or above 480° C., each of these catalysts exhibits substantially the same conversion and selectivity percentages as the 10% CsCl/MgF$_2$ catalyst and exhibits similar impurity levels.

Example 2

About 40 ml of fluorinated 15 wt % Cs$_2$O/MgO catalyst is loaded into the same ¾"×0.035" tube Inconel 625 reactor as described in Example 1 for HCFC-123a dehydrochlorination. The reactor is heated to 480° C. in nitrogen flow. After the temperature is stabilized, 94.6% pure HCFC-123a feed is then passed through the catalyst bed at a rate of 12 grams/hour (g/h). The reactor pressure is set at 1 atm. As shown in Table 2, on average, the 15 wt % Cs$_2$O/MgO catalyst provides a HCFC-123a conversion of about 15% and a CFO-1113 selectivity of about 95%.

TABLE 2

HCFC-123a dehydrochlorination[1]

| Catalyst | Temperature, ° C. | HCFC-123a conv., (%) | Selectivity, % CFO-1113 | others[2] |
|---|---|---|---|---|
| fluorinated 15 wt % Cs$_2$O/MgO | 480 | 15.3 | 95.2 | 4.8 |

[1]Other reaction conditions: 0 psig, 94.6% pure 123a feed, 12 g/h feed rate;
[2]Others include CFO-1112 isomers, HFO-1123, CFC-13, CFC-12, G-124 isomer, etc.

The above experimental protocol is performed using the following catalysts: fluorinated 15 wt % Li$_2$O/MgO, fluorinated 15 wt % Na$_2$O/MgO, and fluorinated 15 wt % K$_2$O/MgO. At or above 480° C., each of these catalysts exhibits substantially the same conversion and selectivity percentages as the fluorinated 15 wt % Cs$_2$O/MgO and exhibits similar impurity levels.

Example 3

40 ml of 1 wt % Pd/MgO catalyst is loaded into the same ¾"×0.035" tube Inconel 625 reactor as described in Example 1 for HCFC-123a dehydrochlorination. The reactor is heated to 450° C. in nitrogen flow. After the temperature is stabilized, 94.6% pure HCFC-123a feed is then passed through the catalyst bed at a rate of 12 grams/hour (g/h). The reactor pressure is set at 1 atm. As shown in Table 3, on average, the 1 wt % Pd/MgO catalyst provides a HCFC-123a conversion of about 10% and a CFO-1113 selectivity of about 97%.

TABLE 3

HCFC-123a dehydrochlorination[1]

| Catalyst | Temperature, ° C. | HCFC-123a conv., (%) | Selectivity, % CFO-1113 | others[2] |
|---|---|---|---|---|
| 1 wt % Pd/MgO | 450 | 10.1 | 97.1 | 2.9 |

[1]Other reaction conditions: 0 psig, 94.6% pure 123a feed, 12 g/h feed rate;
[2]Others include CFO-1112 isomers, HFO-1123, CFC-13, CFC-12, G-124 isomer, etc.

The above experimental protocol is performed using the following catalysts: 1 wt % Pt/MgO, 1 wt % Ru/MgO, 1 wt % Rh/MgO, and 1 wt % Ir/MgO. At or above 450° C., each of these catalysts exhibits substantially the same conversion and selectivity percentages as the 1 wt % Pd/MgO and exhibits similar impurity levels.

What is claimed is:

1. A process for producing chlorotrifluoroethylene (CFO-113) comprising:
   dehydrochlorinating 1,2-dichloro-1,1,2-trifluoroethane (HCFC-123a) in the presence of a catalyst selected from the group consisting of (i) one or more metal halides; (ii) one or more halogenated metal oxides; (iii) one or more zero-valent metals or metal alloys; and (iv) combinations thereof to produce a reaction product comprising CFO-1113, wherein said catalyst comprises at least a catalyst (ii), wherein said catalyst (ii) comprises fluorinated MgO; and from about 5.0 wt. % to about 50 wt % based on the total weight of the catalyst of one or more of a fluorinated Cs$_2$O, a fluorinated Li$_2$O, a fluorinated Na$_2$O, and/or a fluorinated K$_2$O.

2. The process of claim 1 wherein the conversion of HCFC-123a is at least about 5 wt. %.

3. The process of claim 2 wherein a selectivity to chlorotrifluoroethylene is at least about 70 wt. %.

4. The process of claim 3 wherein said reaction product comprises less than about 10 wt. % of CFO-1112.

5. The process of claim 1 wherein the dehydrochlorinating step is conducted at a temperature greater than about 400° C.

6. The process of claim 1 wherein the dehydrochlorinating step is carried out at a temperature of from about 480° C. to about 550° C.

7. The process of claim 1 wherein said catalyst comprises a mono-valent metal halide, a bi-valent metal halide, a tri-valent metal halide, or a combination thereof.

8. The process of claim 1 wherein said catalyst comprises a mono-valent metal halide, a bi-valent metal halide or a combination thereof.

9. The process of claim 1 wherein the catalyst comprises at least one metal halide wherein the component metal is selected from the group consisting of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$, and the component halogen is selected from the group consisting of $F^-$, $Cl^-$, $Br^-$, and $I^-$.

10. The process of claim 1 wherein the catalyst comprises at least one optionally supported metal halide selected from the group consisting of LiF, NaF, KF, CsF, MgF$_2$, CaF$_2$, LiCl, NaCl, KCl, and CsCl.

11. The process of claim 1 wherein the catalyst comprises $MgF_2$ and one or more of CsCl, LiCl, NaCl, KCl, LiF, NaF, KF, and/or CsF.

12. The process of claim 11 wherein the CsCl, LiCl, NaCl, KCl, LiF, NaF, KF, and/or CsF is present in an amount of about 5.0 wt. % to about 50 wt % based on the total weight of the catalyst.

13. The process of claim 1, wherein the catalyst further comprises a halogenated bi-valent metal oxide, a halogenated tri-valent metal oxide, or a combination thereof.

14. The process of claim 1 wherein the catalyst further comprises at least one halogenated metal oxide wherein the component metal is selected from the group consisting $Cr^{3+}$, $Fe^{3+}$, $Ca^{2+}$, $Ni^{2+}$, $Zn^{2+}$, and $Pd^{2+}$.

15. The process of claim 1 wherein the catalyst further comprises at least one fluorinated or chlorinated CaO, chlorinated $Li_2O$, chlorinated $Na_2O$, chlorinated $K_2O$, and chlorinated $Ca_2O$.

16. The process of claim 1 wherein the catalyst further comprises a zero valent metal, a zero valent metal alloy, or a combination thereof.

17. The process of claim 16 wherein the zero valent metal or zero valent metal alloy is optionally supported and comprises at least one metal selected from the group consisting of Pd, Pt, Rh, Ru, Ir, Os, Fe, Co, Ni, Cu, Mo, Cr, Mn, and combinations.

18. The process of claim 16 wherein the zero valent metal or zero valent metal alloy is supported by at least one support selected from the group consisting of MgO, fluorinated MgO, $MgF_2$, carbon materials such as activated carbons and carbon molecular sieves, and $\alpha$-$Al_2O_3$.

19. The process of claim 16 wherein the zero valent metal or zero valent metal alloy comprises one or more of Pd, Pt, Ru, Rh, and/or Ir supported on MgO.

20. The process of claim 19 wherein the Pd, Pr, Ru, Rh, and/or Ir is present in an amount of about 0.05 to about 5 wt % based on the total weight of the catalyst.

21. The process of claim 16, wherein the zero valent metal alloy is present and is selected from the group consisting of alloys 304, 316, 316L, 400, 401, 404, 600, 617, 625, 718, B-2, C-4, C-22, C-276, 800, 825, and combinations thereof.

22. The process of claim 21 wherein the zero valent metal alloy comprises an 800, 825, alloy and combinations thereof.

23. The process of claim 21 wherein the zero valent metal alloy comprises 625 alloy.

* * * * *